(12) United States Patent
Krauss

(10) Patent No.: US 8,413,349 B2
(45) Date of Patent: Apr. 9, 2013

(54) CORRECTIVE INSOLE FOR TREATING DEFECTIVE POSITIONING IN THE METATARSAL AND FOREFOOT AREA

(75) Inventor: Axel Krauss, Munich (DE)

(73) Assignee: Hallufix AG, Munich (DE)

( * ) Notice: Subject to any disclaimer, the term of this patent is extended or adjusted under 35 U.S.C. 154(b) by 406 days.

(21) Appl. No.: 12/648,927

(22) Filed: Dec. 29, 2009

(65) Prior Publication Data
US 2011/0061262 A1 Mar. 17, 2011

(30) Foreign Application Priority Data
Sep. 11, 2009 (DE) .................. 10 2009 041 180

(51) Int. Cl.
*A43B 7/26* (2006.01)
(52) U.S. Cl. .................. 36/94; 36/95; 36/11.5
(58) Field of Classification Search .................. 36/11.5, 36/94, 95, 7.5
See application file for complete search history.

(56) References Cited

U.S. PATENT DOCUMENTS

| | | | | | |
|---|---|---|---|---|---|
| 1,098,397 | A | * | 6/1914 | Pecorella | 602/30 |
| 1,167,019 | A | * | 1/1916 | Reed | 602/30 |
| 1,349,095 | A | * | 8/1920 | Parisi | 602/30 |
| 1,402,375 | A | * | 1/1922 | Parisi | 602/30 |
| 1,746,865 | A | * | 2/1930 | Page | 602/30 |
| 1,943,829 | A | * | 1/1934 | Koomrulan | 36/11.5 |
| 2,297,595 | A | * | 9/1942 | Weinstat | 36/11.5 |
| 3,066,678 | A | * | 12/1962 | Riecken | 36/166 |
| 3,275,002 | A | * | 9/1966 | Scholl | 36/140 |
| 4,745,927 | A | * | 5/1988 | Brock | 36/140 |
| 4,813,162 | A | * | 3/1989 | Harris | 36/88 |
| 2005/0262726 | A1 | * | 12/2005 | Ferniani et al. | 36/8.1 |
| 2009/0113759 | A1 | | 5/2009 | Heid | |
| 2011/0179674 | A1 | * | 7/2011 | Heid | 36/91 |

FOREIGN PATENT DOCUMENTS

| | | |
|---|---|---|
| DE | 1 261 778 | 2/1968 |
| DE | 30 49 528 | 7/1982 |
| WO | WO-2010/003531 | 1/2010 |

* cited by examiner

*Primary Examiner* — Marie Patterson
(74) *Attorney, Agent, or Firm* — Jordan and Hamburg LLP

(57) ABSTRACT

A corrective insole for treating defective positioning in the metatarsal and forefoot areas of the foot which includes an insole including at least two strap mechanisms a toe strap and a metatarsal strap such that the metatarsal strap encircles the metatarsal area of the foot to enable optimum correction of defective positioning associated with conditions such as hallux valgus.

12 Claims, 4 Drawing Sheets

CORRECTIVE INSOLE FOR TREATING DEFECTIVE POSITIONING IN THE METATARSAL AND FOREFOOT AREA

BACKGROUND OF THE INVENTION

The invention relates to a corrective insole for treating defective positioning in the metatarsal and forefoot areas of the foot.

Such defective positioning, such as hallux valgus, hammer toes, or claw toes, sometimes occurs due to hereditary abnormalities and sometimes due to faulty footwear or overloading or malpositioning of the lower extremities. The following explanations are limited relate to widespread malpositioning known as hallux valgus, and are also applicable to other types of defective positioning in the metatarsal and forefoot area. Hallux valgus is defined as an outward deviation of the big toe at the metatarso-phalangeal joint. The term, "outward" here and in the following always indicates a direction away from the center plane of the body; specifically towards the small toe. Consequently, the term, "inward" is in the opposite direction, that is, from the small toe towards the big toe. In hallux valgus, the tendons of the toes no longer run centrally across the joint, but rather run further inward, and they pull the toes into a slanted position relative to each other. The ball of the big toe, which projects because of this slanted positioning, frequently suffers painful inflammation, caused by the pressure of the shoe in this area. At the same time, the angle between the various metatarsal bones is enlarged, especially between the metatarsal bone adjacent to the big toe and the proximal phalanx of the big toe. A frequent accompanying symptom is arthrosis. Among the causes of hallux valgus are splay foot, with the anterior transversal arch caving in and the big toe deviating as a result, and especially faulty footwear, which, due to fashion, is frequently worn in a size that is too small, has heels that are too high, or has a toe area that is too narrow.

In addition to surgical treatment, orthopedic measures such as special splints or corrective insoles are customary for correcting hallux valgus.

One such corrective insole is known from DE 20 2004 006 113 U1. This publication describes an insole that in the toe area has an elastic strap that is guided through a slit in the sole. This strap can be stretched about the big toe such that it brings it into a position required for correcting hallux valgus.

The aforementioned insole it is disadvantageous since it only corrects defective positioning of the big toe itself. This is not sufficient for effective and lasting correction of defective positioning described above since there is no change in the angular position of all the metatarsal bones.

Thus, it is desired to provide a corrective insole that attains improved and comprehensive correction of defective positioning of all of the foot bones with respect to the conditions described.

SUMMARY OF THE INVENTION

Herein, the term "corrective insole" refers to an "insole" and the strap mechanisms shown attached thereto, "insole" then refers only to a sole without any additional components.

Correction of the defective positioning described above is achieved by providing multiple stretchable strap mechanisms which are arranged and guided through openings in the insole.

The invention is based on the understanding that to completely correct the defective positioning, especially for hallux valgus, the angular position must be changed and maintained not only for the metatarsal bone of the big toe, but also for the metatarsal bones of the toes adjacent thereto. Such correction is provided by the invention in that an adjustable, correcting force is exerted on the metatarsal bones in the center area of the corrective insole by using a stretchable and fixable strap mechanism, which is especially in contact with the area of the foot above which the associated metatarsal bones are positioned when it is worn. This force, together with the force exerted on the big toe by the strap mechanism in the big toe area, effects an optimum change in the angular position of the bones involved in that it pivots the big toe inward and pivots the associated metatarsal bones outward. This converts the incorrect positioning of the two adjacent bones relative to one another to a correct, aligned orientation. Particularly advantageous is the provided step-less adjustment of each strap mechanism provided by, for instance, a velcro fastener, which permits the force, and thus the angular position of the body parts involved, to be finely adjusted. In accordance with the invention, the position of the big toe and its bones and the position of the metatarsal bones can be adjusted separately because the two strap mechanisms can be actuated independently of one another.

An advantageous embodiment of the corrective insole herein comprises the additional strap mechanism being arranged such that when the corrective insole is worn, the foot is kept in contact with the strap of the strap mechanism so as to maintain contact between the insole at the back of the foot and at the sides and also at the portion of the sole beneath the strap. This avoids the foot being pressed flat onto the insole, which would act against correcting the hallux valgus because the metatarsal bones are spread even more by this. Instead, the encirclement of the metatarsal area ensures that these bones in this area are subjected to a force directed to the center of the foot so as to bundle them together. Thus, this area of the foot becomes rounded, rather than flattened, by the force of the strap. This effect is attained in accordance with the invention in that the strap of the additional strap mechanism is conducted via longitudinal openings that are disposed essentially parallel to one another at the same longitudinal position of the insole and that are clearly offset from the center of the insole relative to the adjacent lateral edge of the insole. They thus come to be disposed beneath the sole of the foot when the corrective insole is worn so that the associated strap encircles the foot.

In further advantageous embodiments, there can be three openings associated with each strap of the additional strap mechanism that are arranged parallel to one another relative to their longitudinal extension. One end of the strap is conducted through an opening, preferably the opening located on the outside of the insole, and is fixed to the bottom of the insole. This is achieved by using an appropriate embodiment of the end, for instance a thickening that engages in a positive fit and/or non-positive fit with the opening, which is specially shaped for this purpose, when the strap is threaded through from the bottom. Naturally this end could also be securely or detachably connected to the insole by other means or measures. For example, it would be possible to use rivets or adhesive or a velcro fastener. The free end of the strap is conducted through a second opening, forming a loop for the foot, and this second opening must also be disposed beneath the sole of the foot. The strap runs from here beneath the insole to the third opening, through which it exits upward and at its free end can be gripped, stretched, and fixed on a looped surface thereof the top of the foot. In accordance with the invention, a velcro fastener is preferably used for fixing it when it is stretched because such a fastener can be displaced and fixed in a stepless manner. Naturally other types of fixation are also possible, such as for instance buckles, ratchet-like fasteners, or snaps.

In one modification of the invention, an embodiment having only two openings for the strap is provided. The free end of the strap is not conducted through a third opening as in the first exemplary embodiment of the invention. Instead, after passing through the second opening, it is conducted upward from the bottom of the insole around the adjacent outer edge and is fixed there after stretching so as to grip against such outer edge.

The construction provided by the invention is also useful for treating hammer toes or claw toes. The openings in the insole are distributed for this purpose across the width of the toe area and can be fitted with strap mechanisms depending on the correction needed. Here and in the rest of the description, strap mechanism always means a stretchable strap having one fixed secure end and one fixable and detachable free end configured to provide at least one loop for a part of the foot to pass through, and specifically the metatarsal area of the foot or a toe, and which is provided by conducting the free end through the associated openings in the insole.

The insole preferably has areas of different hardness such that it is embodied harder and more stable in the area of the openings adjacent each strap mechanism relative to the other areas. This ensures that the insole is sufficiently stable in the area of the strap mechanisms to absorb the forces necessary for correcting the defective positioning. In addition, the insole should be soft and flexible as desired in the other areas. Thus, the flexibility in the longitudinal direction of the insole that is necessary for the foot to roll when walking is attained by providing a relatively soft and flexible area arranged between the metatarsal area and the forefoot/toe area. This intermediate area and the likewise softened and flexible heel area of the insole enhance wearing comfort.

Preferably, plastic is employed as the material for the inventive corrective insole, as it is particularly suitable for cost-effective production using injection molding and is available in numerous modified forms, such as solid or foamed material. Different types of materials can be combined for the different areas of the insole, including different modifications of the material can be arranged adjacent to one another. In addition to pure plastics, such as polyurethane or ethylene vinyl acetate (EVA), it is also possible to have combinations with other materials such as cork, leather, and metal inlays.

In another preferred embodiment, an orthotic sole, which is understood as a sole with a special shape for the foot bed so as to effect therapeutic action on the foot, is used for the insole. Particularly preferred is a proprioceptive orthotic sole, such a sole being understood to have a stimulating effect on certain nerves or nerve centers due to a special arrangement and shape of elements provided in the foot bed. This causes signals to be produced in the brain that lead to beneficial reactions in the muscular system. Details can be found for instance at the Internet site www.podoorthesiologie.de.

The inventive corrective insole is used whereby the foot is inserted into the loops of the corrective insole and then the straps are stretched by pulling their free ends and fixed, by means of the fastener, in the desired position, i.e., the position necessary for the correction. This happens outside of the shoe for which the corrective sole is provided. After the two straps in the strap mechanism have been adjusted, the foot, together with the corrective insole, are inserted into the shoe, which is then laced or held on the foot in some other manner determined by its design.

BRIEF DESCRIPTION OF THE DRAWINGS

FIG. 1 is a schematic depiction of a corrective insole 1 in accordance with the invention. The corrective insole 1 includes the insole 2, which has a foot bed 3 that is preferably configured according to orthopedic principles. The insole 2 is divided into a front toe area 4, a metatarsal area 5, and a heel or rear foot area 6, which merge seamlessly into one another and which are defined by the anatomy of the foot. The insole 2 has an outer edge 7 and an inner edge 8, "inner" and "outer" being defined as is normal with respect to the center body plane, as well as a bottom 9.

Figure 1:
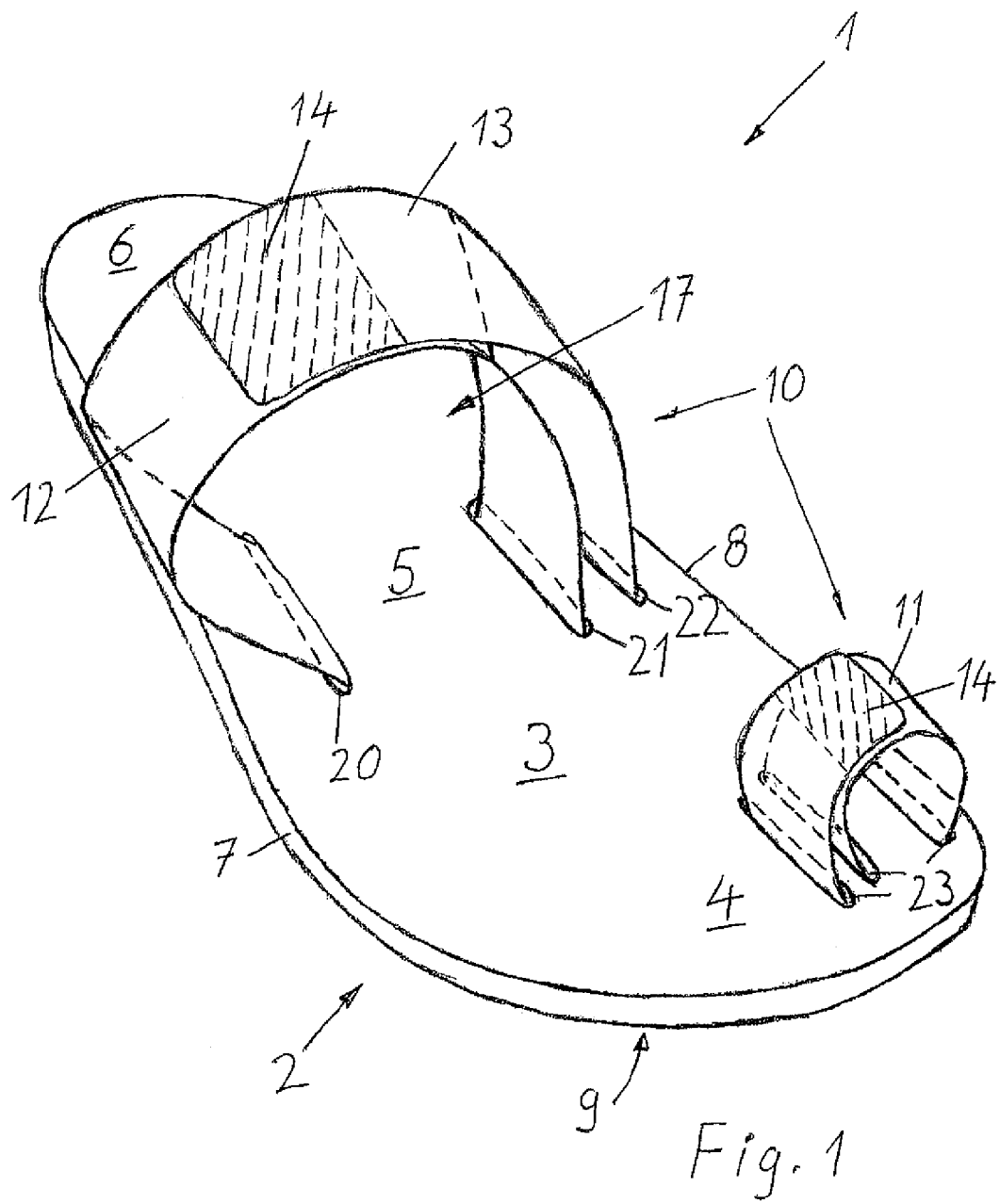
FIG. 1 depicts a corrective insole in accordance with the invention.

The insole 2 is fitted with at least two separate strap mechanisms 10, including the toe strap 11 and the metatarsal strap 12, their designations resulting from their respective positions on the foot bed 3. For receiving, conducting, and fixing each of the straps 11 and 12, the insole 2 is provided with a plurality of longitudinal openings 20, 21, 22, 23 that are conducted from the foot bed 3 through the entire thickness of the insole to its bottom. The shape of the openings 20, 21, 22, 23 is adapted to the thickness and width of the straps 11, 12 in the strap mechanisms 10, the longitudinal extension of the openings 20, 21, 22, 23 normally coinciding at least approximately with the longitudinal extension of the insole 2. However, it is also possible to have deviations from this for special corrections necessary to address a particular condition.

Each of the toe strap 11 and the metatarsal strap 12, referred to hereinafter as "strap" since the construction is the same for the two straps, has a free end 13 on which a fastener is arranged that makes it possible to fix the strap 11, 12, after stretching, about the respective area of the foot. This fastener is depicted in FIG. 1 as a velcro fastener 14, which is preferred for this application because it enables stepless and secure fixation of the strap. The other end area 15 of each of the straps 11, 12 is conducted from below through a first opening 20 in the insole 2 and fixed in or in the vicinity of this opening 20, as explained herein. The strap is conducted out from here, forming a loop 17 for the foot to pass through above the foot bed 3, and again passes into the insole 2 through a second opening 21. The strap 11, 12 is reversed behind, i.e., passed under a portion of the insole which is adjacent the second opening 21 on the bottom 9 of the insole 2 and passes therethrough from below through a third opening 22. The end 13 of the strap 11, 12, still free, is thus disposed above the insole 2 and can be grasped from there in order to effect the stretching and subsequent fixation necessary for the correction.

Figure 4:
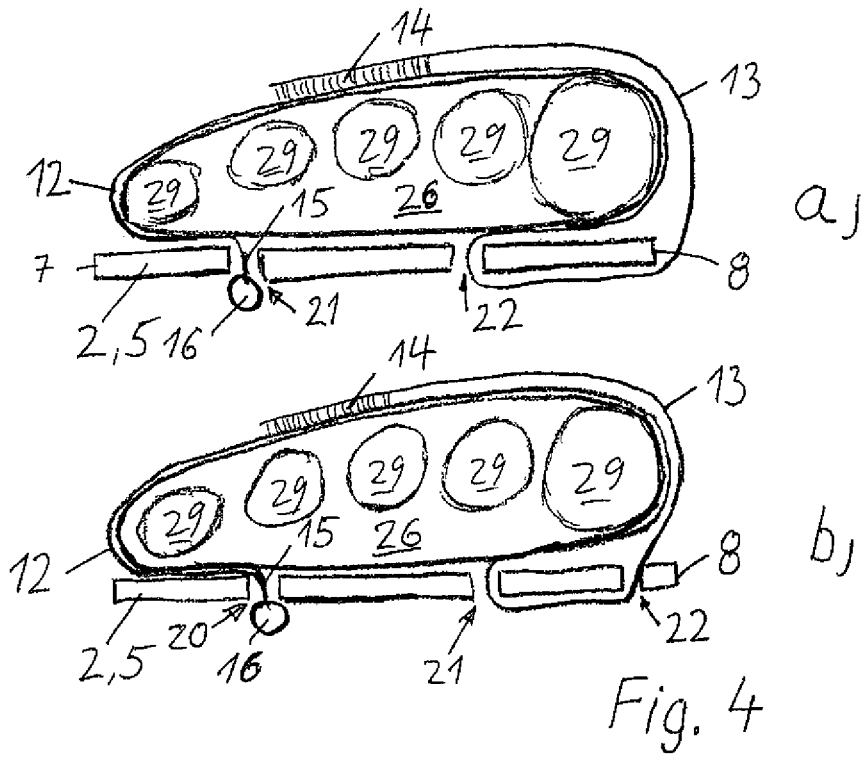
FIGS. 4a and 4b depict a cross-section through the metatarsal area with the corrective insole positioned thereon.

In accordance with the invention, the first and second openings 20 and 21 in the metatarsal area 5 are clearly arranged at a distance from the adjacent edges, outer edge 7 and inner edge 8, of the insole 2, as can be seen more clearly in FIGS. 4a and 4b. These distances should be at least 10% of the width of the insole 2 in the metatarsal area, a figure in the range of 15% to 45% of this width being preferred. What this attains is that the metatarsal area of the foot 26 (see FIGS. 4a and 4b) experiences a force that acts essentially radially inward, because this area is almost completely enclosed by the metatarsal strap 12. The force oriented in this manner is essential for correcting the defective positioning of the metatarsal bones, because the force bundles them, instead of pressing them apart as would be the case if the strap engaged only on the lateral edges 7, 8 of the insole 2.

Figure 2:
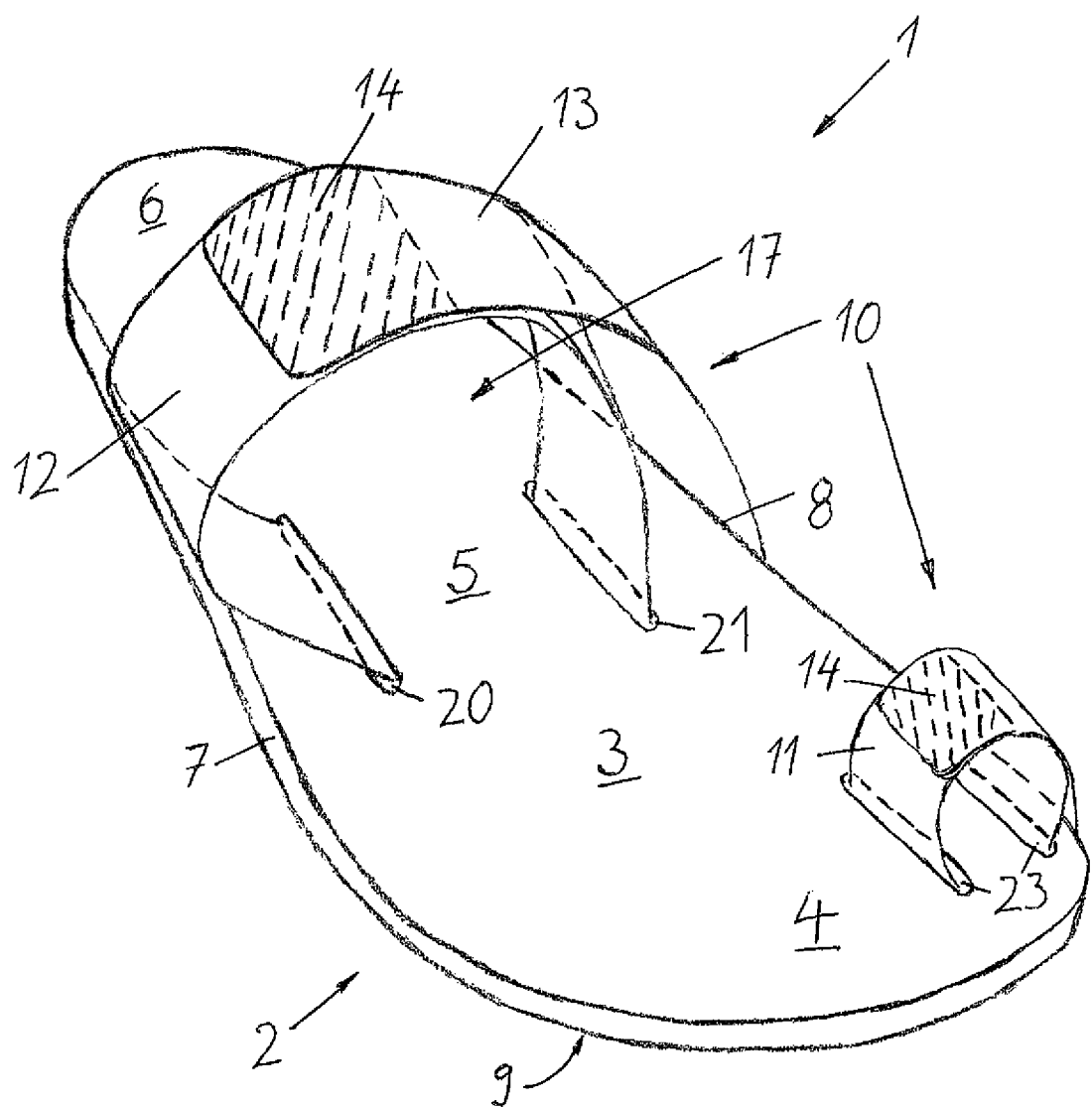
FIG. 2 depicts another exemplary embodiment of a corrective insole in accordance with the invention.

FIG. 2 depicts a modified embodiment of the invention in which the insole 2 has only two openings 20 and 21 for the associated strap 11, 12. After exiting through the second opening 21 on the bottom 9 of the insole 2, the free end of the strap 11 or 12 is reversed along the bottom of the insole 2 and encloses the adjacent edge of the insole 2, here the inner edge 8, so as to grip against the edge 8 before it reaches the top of the corrective insole 1. The other details coincide with the exemplary embodiment in accordance with FIG. 1.

Figure 3:
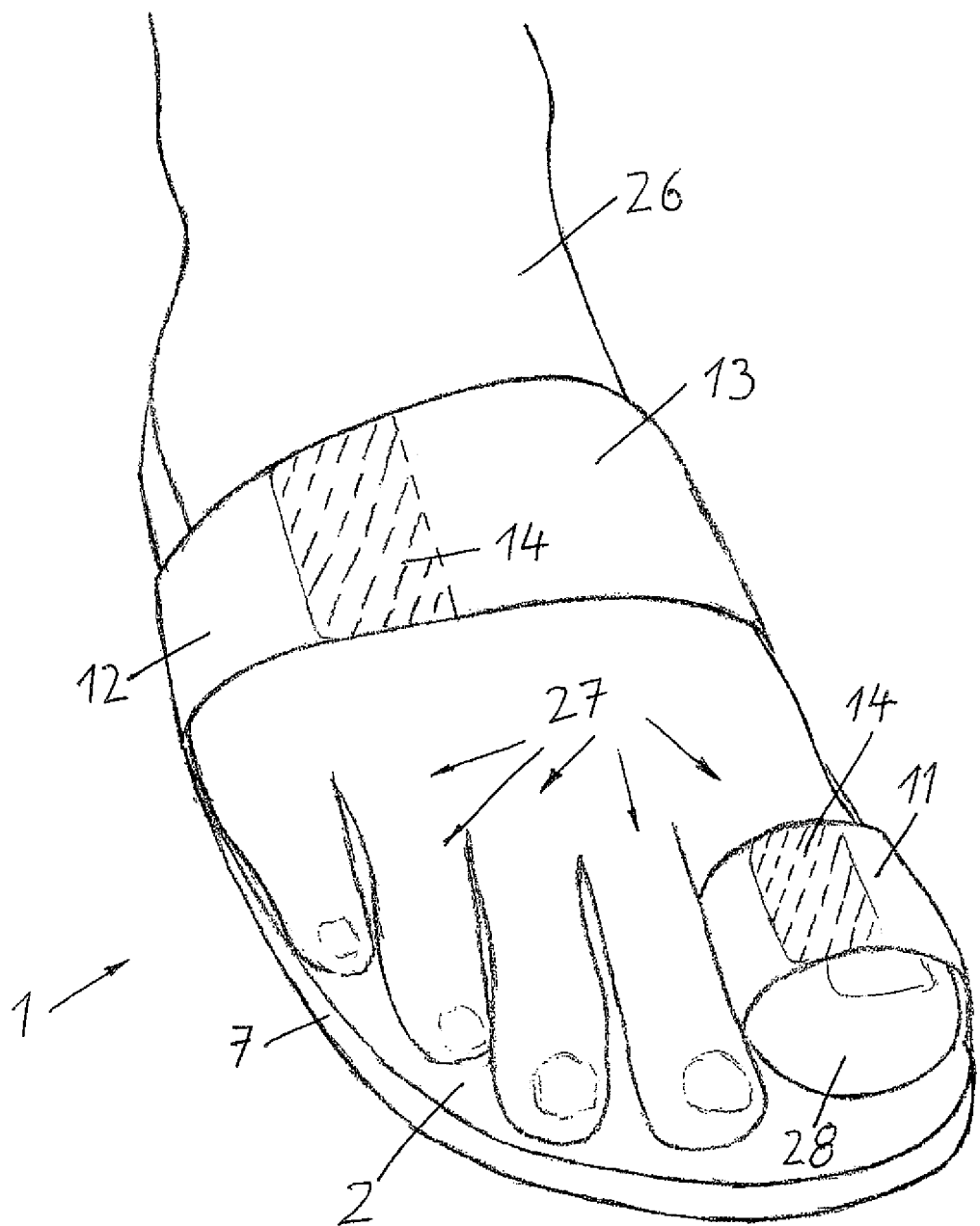
FIG. 3 is an elevation of a human foot with a corrective insole in accordance with the invention.

FIG. 3 depicts a corrective insole 1 in accordance with the invention arranged on a human foot 26. The foot 26 is inserted with the applied and correctly stretched and fixed corrective insole 1 into the shoe (not shown), which can then be laced in the usual fashion.

FIGS. 4a, b are schematic cross-sections of the metatarsal area of a human foot 26 with an applied and stretched corrective insole 1, specifically in accordance with the exemplary embodiment in accordance with FIGS. 1,4b and in accordance with FIG. 2 and FIG. 4a respectively. The reference numbers here have the same meaning as in the other figures. In particular in FIG. 4b, the three openings 20, 21, and 22 and how the metatarsal strap 12 is conducted from the first opening 20 as a loop 17 about the metatarsal area of the foot to the second opening 21 and from there through the third opening 22 to the top of the insole 2 are shown. For the purpose of clarification, the velcro fastener 14 on the free end 13 of the metatarsal area 12 is shown not yet fixed. The other end of the metatarsal strap 12 which is secured to the insole 2 has a thickening 16 on its outermost end area 15 that fixes this end in the associated first opening 20, since this opening 20 is configured too narrow for the thickening 16 to pass through. Such fixing of the one strap end to the insole 2 using a positive fit and/or non-positive fit is naturally also possible using other means, such as gluing, a velcro fastener, or rivets.

FIG. 4a depicts the other embodiment of the corrective insole 1, having only two openings 20 and 21 in the insole 2 for the metatarsal strap 12 to pass through. In this variant, this free end 13 is conducted about the inner edge 8 of the insole 2 and then is fixed on the top by means of the velcro fastener 14.

Figure 5:
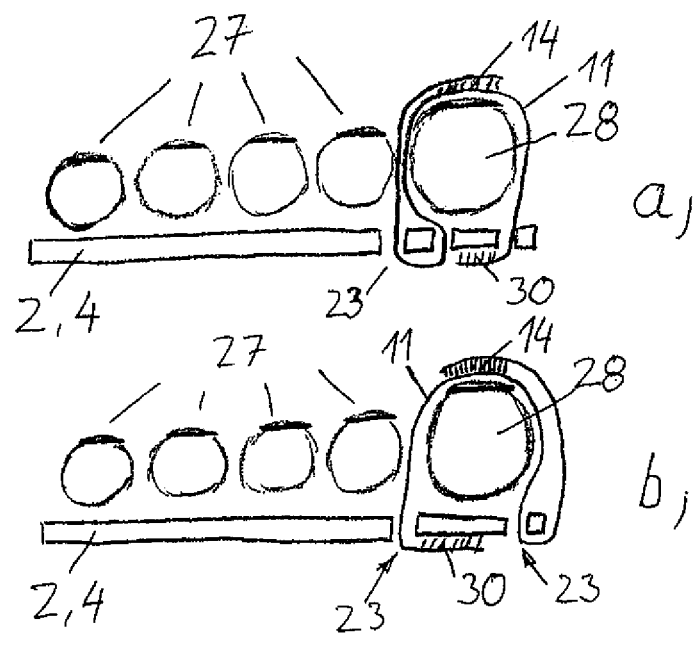
FIGS. 5a and 5b depict a cross-section through the toe area with the corrective insole positioned thereon.

FIGS. 5a, b provide a schematic depiction of a cross-section through the toe area of the human foot with the applied corrective insole 1, and show a strap mechanism 10 having a toe strap 11 being present only in the area of the big toe 28. The toe band 11 is conducted completely like that for the metatarsal area in FIGS. 4a and 4b, with the single difference that the one secure end of the toe strap here is fastened by means of adhesive 30, indicated here, or a velcro fastener, to the bottom 9 of the insole 2. It is understood that in accordance with the invention further openings 23 for strap mechanisms 10, 11 can be present in the area of the other toes 27 so that these toes 27 can also be subjected to a corrective displacement, individually or in groups.

The invention claimed is:

1. A corrective insole for treating defective positioning in the metatarsal and forefoot areas, comprising:
an insole;
a strap mechanism that is conducted through openings in said insole and that exerts a correcting force on at least the big toe at a respective area of said insole; and
a metatarsal stretchable strap mechanism conducted via openings in said insole that is arranged in the area of the metatarsal bones,
the insole comprising at least two longitudinally extending openings relative to a longitudinal axis of the insole that are positioned at the metatarsal foot area of the insole and spaced from lateral edges of the insole so, that the metatarsal strap mechanism, when assembled with the insole, is passed through said at least two openings in order to partially encircle a bottom portion of a foot in the metatarsal foot area so as to maintain contact between the bottom portion of the foot and the metatarsal strap mechanism when the corrective insole is worn, and in which
each of the strap mechanism that exerts a corrective force on at least the big toe and the metatarsal stretchable strap mechanism comprise a separate strap mechanism that is respectively positioned and contained within a plane that is transverse to the longitudinal axis of the insole, the respective planes containing the separate strap mechanisms being spaced and parallel to one another.

2. The corrective insole in accordance with claim 1, wherein said metatarsal strap mechanism is conducted through a third opening in said metatarsal area of said insole.

3. The corrective insole in accordance with claim 2, wherein each of said strap mechanisms comprises a flexible strap with a fastener at a free end thereof for stretching and fixing the strap mechanism, and is connected to said insole an end thereof opposing said free end.

4. The corrective insole in accordance with claim 3, wherein the opposing end comprises a thickened portion which can engage said insole at one of said openings in said insole so as to enable said connection therewith.

5. The corrective insole in accordance with claim 4, wherein at least three openings are provided for said strap mechanism exerting said force on said big toe.

6. The corrective insole in accordance with claim 5, wherein said at least three openings are arranged distributed over the width of said toe area and can be fitted with one or a plurality of strap mechanisms.

7. The corrective insole in accordance with claim 6, wherein said insole has areas of different hardness.

8. The corrective insole in accordance with claim 5, wherein the areas of said insole that have said openings for said strap mechanisms are embodied harder than the other areas of said insole.

9. The corrective insole in accordance with claim 8, wherein said insole comprises an injection-molded plastic.

10. The corrective insole in accordance with claim 9, wherein said insole comprises an orthotic sole for aligning the metatarsal and forefoot areas.

11. The corrective sole in accordance with claim 10, wherein said insole comprises on its bottom another rigid or flexible sole.

12. A sandal for correcting defective positioning in the metatarsal and forefoot areas in accordance with claim 11.

* * * * *